United States Patent
Suzuki et al.

(10) Patent No.: US 8,907,080 B2
(45) Date of Patent: Dec. 9, 2014

(54) PROCESS FOR IMPARTING WATER SOLUBILITY OR WATER DISPERSIBILITY TO HYDROPHOBIC CLUSTER COMPOUND

(75) Inventors: Toshio Suzuki, Osaka (JP); Hideaki Ueda, Osaka (JP); Takeshi Nagasaki, Osaka (JP); Mitsunori Kirihata, Osaka (JP); Munenori Numata, Kyoto (JP); Atsushi Ikeda, Nara (JP)

(73) Assignees: Daiso Co., Ltd., Osaka (JP); Osaka City University, Osaka (JP); Osaka Prefecture University Public Corporation, Osaka (JP); Kyoto Prefectural Public University Corporation, Kyoto (JP); National University Corporation Nara Institute of Science and Technology, Nara (JP)

( * ) Notice: Subject to any disclaimer, the term of this patent is extended or adjusted under 35 U.S.C. 154(b) by 196 days.

(21) Appl. No.: 13/511,253

(22) PCT Filed: Nov. 26, 2010

(86) PCT No.: PCT/JP2010/071128
§ 371 (c)(1),
(2), (4) Date: Jun. 29, 2012

(87) PCT Pub. No.: WO2011/065481
PCT Pub. Date: Jun. 3, 2011

(65) Prior Publication Data
US 2012/0264931 A1      Oct. 18, 2012

(30) Foreign Application Priority Data
Nov. 27, 2009 (JP) ................. 2009-270801

(51) Int. Cl.
C08B 37/00 (2006.01)
B82Y 40/00 (2011.01)
C07H 23/00 (2006.01)
C01B 31/02 (2006.01)
B82Y 30/00 (2011.01)
C08L 5/00 (2006.01)

(52) U.S. Cl.
CPC ............. C01B 31/0273 (2013.01); B82Y 30/00 (2013.01); B82Y 40/00 (2013.01); C08B 37/0057 (2013.01); C08L 5/00 (2013.01); Y10S 977/734 (2013.01); Y10S 977/742 (2013.01)
USPC ....... 536/123.12; 536/121; 977/734; 977/742

(58) Field of Classification Search
None
See application file for complete search history.

(56) References Cited

FOREIGN PATENT DOCUMENTS

| JP | 2005-104762 | 4/2005 |
|---|---|---|
| JP | 2006-069812 | 3/2006 |
| JP | 2006-205302 | 8/2006 |
| JP | 2007-238847 | 9/2007 |
| JP | 2008-222585 | 9/2008 |

OTHER PUBLICATIONS

Sakurai et al. Chem. Commun., 2005, 4383-4398.*
Atta-ur-Rahman, Studies in Natural Products Chemistry, vol. 23, Elsevier, 2000, p. 118.*
Bohn et al. Carbohydrate Polymers 28 (1995) 3-14.*
Sigma-Aldrich product page for Congo Red, downloaded from the internet Apr. 7, 2014.*
JP 2005-104762, 2005, machine translation.*
JP 2007-238847, 2007, machine translation.*
JP 2006-205302, 2006, machine translation.*
English translation of International Preliminary Report on Patentability and Written Opinion dated Jul. 10, 2012.
International Search Report issued Dec. 21, 2010 in International (PCT) Application No. PCT/JP2010/071128, of which the present application is the national stage.

* cited by examiner

*Primary Examiner* — Layla Bland
(74) *Attorney, Agent, or Firm* — Wenderoth, Lind & Ponack, L.L.P.

(57) ABSTRACT

Provided is a complex comprising a hydrophobic cluster compound and a β-1,3-1,6-D-glucan having a degree of branching (a ratio of β-1,6 linkages to β-1,3 linkages) of 50 to 100%.

9 Claims, 7 Drawing Sheets

(A)

(B)

(A)

(B)

(A)

(B)

PROCESS FOR IMPARTING WATER SOLUBILITY OR WATER DISPERSIBILITY TO HYDROPHOBIC CLUSTER COMPOUND

This application is a U.S. national stage of International Application No. PCT/JP2010/071128 filed Nov. 26, 2010.

TECHNICAL FIELD

The present invention relates to a water-soluble or water-dispersible complex comprising a hydrophobic cluster compound, a production process therefor, and a process for imparting water solubility or water dispersibility to a hydrophobic cluster compound.

BACKGROUND ART

Among hydrophobic cluster compounds, non-metal cluster compounds have been administered to a living body on a trial basis for tumor treatment or the like in recent years.

For example, a fullerene, a carbon cluster compound, has been attempted to be used as a photosensitizer in photodynamic therapy, in which a photosensitizer absorbed by tumor cells or by neovascular endothelial cells in tumor tissue is exposed to laser beam irradiation, thereby generating active oxygen to destroy the tumor cells and to eventually eliminate the tumor.

A carborane, a boron cluster compound, has also been attempted to be used as a boron compound in boron neutron capture therapy, in which a boron compound accumulated in tumor cells is exposed to thermal neutron irradiation, thereby emitting α rays to destroy nearby tumor cells.

Metal cluster compounds are conductive or semiconductive and hence in atomized form can be used to realize a wiring method which involves applying such a compound and which can be a substitute for a conventional plating wiring. Therefore application of metal cluster compounds has been investigated in various areas including circuit formation for electronic or information devices and the development of sensors, which investigation has contributed to the development of one aspect of printable electronics technology.

Carbon nanotubes are highly conductive and, since they are carbon compounds, are highly environmentally friendly. With these advantages, carbon nanotubes are expected to be applied to conductive carriers or devices.

For the purpose of administering a non-metal cluster compound that is among hydrophobic cluster compounds to a living body, it is necessary to solubilize the compound. For example, JP 2007-238847 A discloses that a fullerene can be made soluble in water by complexation with a β-1,3-1,6-glucan having a low degree of branching with β-1,6-linked side chains, such a β-1,3-1,6-glucan being exemplified by sizofuran. JP 2006-69812 A discloses that a fullerene can be made soluble in water by complexation with cyclodextrin (α-glucan). JP 2008-222585 A discloses that a carborane can be made soluble in water by complexation with sizofuran. JP 2005-104762 A discloses that a carbon nanotube can be made soluble in water by complexation with sizofuran.

However, these complexes comprising a non-metal cluster compound lack sufficient water solubility for practical use. The complexes also lack sufficient dispersibility in aqueous solutions. These properties make handling of the complexes difficult.

Regarding a metal cluster compound that is among hydrophobic cluster compounds, particles of a metal cluster compound existing not independently but forming a regular structure exhibit novel electronic, optical, magnetic properties that cannot be observed when the particles independently exist. Various studies for applying such novel properties to advanced electronics, optical devices, and the like have been actively conducted in recent years. However, since there are no specific interactions between metal cluster compound particles, the particles hardly aggregate in a self-organized manner. In contrast, a high-molecular chain has a particular higher-order structure formed in a self-organized manner and is capable of serving for aggregation or dispersion of independently existing metal cluster compound particles. For example, JP 2006-205302 A discloses that gold can be made soluble and dispersible in water by complexation with sizofuran. However, such a complex containing a metal cluster compound lacks sufficient water dispersibility and water solubility for practical use.

SUMMARY OF INVENTION

Technical Problem

An object of the present invention is to provide a hydrophobic cluster compound complex having sufficient water solubility or water dispersibility for practical use, an efficient production process therefor, and a process for imparting sufficient water solubility or water dispersibility for practical use to a hydrophobic cluster compound.

Solution to Problem

The inventors have conducted extensive studies in order to solve the above problems and found out that the water solubility or water dispersibility of a hydrophobic cluster compound can be remarkably increased when the compound is complexed with β-1,3-1,6-D-glucan, in particular, a β-1,3-1, 6-D-glucan in which the ratio of β-1,6 linkages constituting side chains to β-1,3 linkages constituting the main chain (the degree of branching) is 50 to 100%.

The present invention has been completed based on this finding and provides the hydrophobic cluster compound complex described below, a production process therefor, and a process for imparting water solubility or water dispersibility to a hydrophobic cluster compound.

(1) A complex comprising a hydrophobic cluster compound and a β-1,3-1,6-D-glucan having a degree of branching (a ratio of β-1,6 linkages to β-1,3 linkages) of 50 to 100%.

(2) The complex according to (1), wherein the hydrophobic cluster compound contains at least one kind of non-metal atom selected from the group consisting of boron, carbon, silicon, sulfur, and phosphorus.

(3) The complex according to (2), wherein the hydrophobic cluster compound is a carborane, a fullerene, a carbon nanotube, or a carbon nanocoil.

(4) The complex according to (1), wherein the hydrophobic cluster compound contains at least one kind of metal atom selected from the group consisting of platinum, gold, silver, copper, titanium, zinc, iron, cobalt, magnesium, aluminum, and zirconium.

(5) A production process for a complex comprising a hydrophobic cluster compound and a β-1,3-1,6-D-glucan, the process comprising the steps of agitating a hydrophobic cluster compound with a β-1,3-1,6-D-glucan having a degree of branching (a ratio of β-1,6 linkages to β-1,3 linkages) of 50 to 100% while maintaining the solid state, and agitating the mixture with added water.

(6) The process according to (5), wherein the hydrophobic cluster compound is a carborane, a fullerene, a carbon nanotube, or a carbon nanocoil.

(7) The process according to (5), wherein the hydrophobic cluster compound contains at least one kind of metal atom selected from the group consisting of platinum, gold, silver, copper, titanium, zinc, iron, cobalt, magnesium, aluminum, and zirconium.

(8) A production process for a complex comprising a hydrophobic cluster compound and a β-1,3-1,6-D-glucan, the process comprising the steps of mixing, in a polar solvent, a hydrophobic cluster compound and a β-1,3-1,6-D-glucan having a degree of branching (a ratio of β-1,6 linkages to β-1,3 linkages) of 50 to 100%, and adding water to the obtained mixture and allowing the mixture to ripen.

(9) The process according to (8), wherein the hydrophobic cluster compound is a carborane, a fullerene, a carbon nanotube, or a carbon nanocoil.

(10) The process according to (8), wherein the hydrophobic cluster compound contains at least one kind of metal atom selected from the group consisting of platinum, gold, silver, copper, titanium, zinc, iron, cobalt, magnesium, aluminum, and zirconium.

(11) A process for imparting water solubility or water dispersibility to a hydrophobic cluster compound, the process comprising the steps of agitating a hydrophobic cluster compound with a β-1,3-1,6-D-glucan having a degree of branching (a ratio of β-1,6 linkages to β-1,3 linkages) of 50 to 100% while maintaining the solid state, and agitating the mixture with added water.

(12) The process according to (11), wherein the hydrophobic cluster compound is a carborane, a fullerene, a carbon nanotube, or a carbon nanocoil.

(13) The process according to (11), wherein the hydrophobic cluster compound contains at least one kind of metal atom selected from the group consisting of platinum, gold, silver, copper, titanium, zinc, iron, cobalt, magnesium, aluminum, and zirconium.

(14) A process for imparting water solubility or water dispersibility to a hydrophobic cluster compound, the process comprising the steps of mixing, in a polar solvent, a hydrophobic cluster compound and a β-1,3-1,6-D-glucan having a degree of branching (a ratio of β-1,6 linkages to β-1,3 linkages) of 50 to 100%, and adding water to the obtained mixture and allowing the mixture to ripen.

(15) The process according to (14), wherein the hydrophobic cluster compound is a carborane, a fullerene, a carbon nanotube, or a carbon nanocoil.

(16) The process according to (14), wherein the hydrophobic cluster compound contains at least one kind of metal atom selected from the group consisting of platinum, gold, silver, copper, titanium, zinc, iron, cobalt, magnesium, aluminum, and zirconium.

Advantageous Effects of Invention

The present invention makes it possible to impart water solubility to a hydrophobic cluster compound, which is a relatively large compound, and thereby to disperse or dissolve the compound in water.

Since the β-1,3-1,6-D-glucan employed in the present invention for making a hydrophobic cluster compound soluble or dispersible in water is a component that is also used in food, the complex of the present invention is highly safe and can be applied to a medicine. The complex of the present invention can also be used for various applications such as catalyst materials, magnetic recording materials, conductive film forming materials, semiconductor film forming materials, and pigments.

BRIEF DESCRIPTION OF DRAWINGS

FIG. 3 (B) is a UV-Vis-NIR spectrum of an aqueous AQUA β-fullerene (C60) complex solution.

FIG. 4 (B) is a UV-Vis-NIR spectrum of an aqueous AQUA β-fullerene (C70) complex solution.

FIG. 5 (B) is a graph showing that the body weight of tumor bearing mice was not reduced by the administration of an aqueous AQUA β-fullerene (C70) complex solution followed by light irradiation. The arrows in FIGS. 5 (A) and (B) indicate light irradiation.

DESCRIPTION OF EMBODIMENTS

Figure 1:
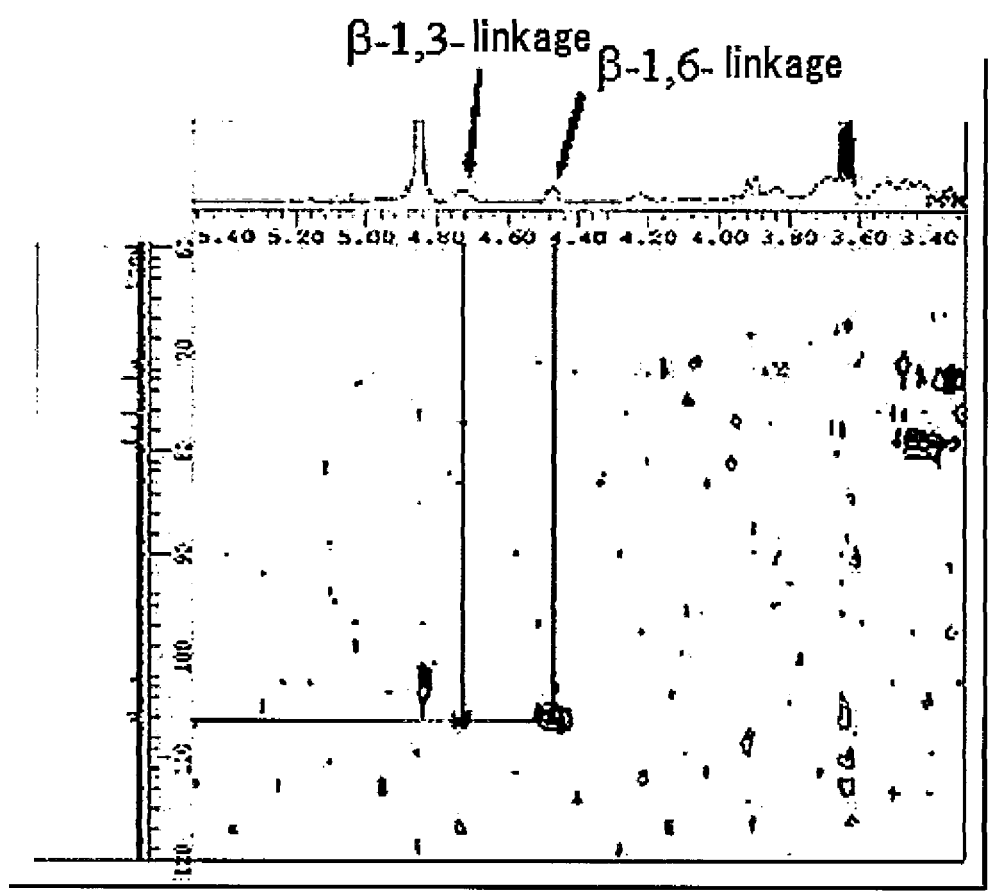
FIG. 1 is a $^1$H NMR spectrum of the *Aureobasidium pullulans*-derived glucan obtained in Example below.

The present invention will be described in detail below.
(1) Complex

The complex of the present invention comprises a hydrophobic cluster compound and a β-1,3-1,6-D-glucan in which the ratio of β-1,6 linkages constituting side chains to β-1,3 linkages constituting the main chain (the degree of branching) is 50 to 100%.
(1-1) Hydrophobic Cluster Compound The cluster compound of the present invention refers to a group or a microparticle formed by the aggregation of a few to a few hundred atoms or molecules. The hydrophobic cluster compound herein refers to a cluster compound having a water solubility at 25° C. of, for example, 10 mg/mL or less, preferably 5 mg/mL or less, more preferably 3 mg/mL or less, further preferably 1 mg/mL or less. Examples of the hydrophobic cluster compound include a metal cluster compound containing one or more kinds of metal atoms such as lead (Pb), nickel (Ni), iron (Fe), magnesium (Mg), cobalt (Co), rhodium (Rh), ruthenium (Ru), platinum (Pt), gold (Au), silver (Ag), copper (Cu), titanium (Ti), zinc (Zn), palladium (Pd), indium (In), gallium (Ga), germanium (Ge), aluminum (Al), and zirconium (Zr), or oxides or sulfides thereof; and a non-metal cluster compound containing one or two kinds of non-metal atoms such as boron (B), carbon (C), silicon (Si), sulfur (S), and phosphorus (P). The hydrophobic cluster compound of the present invention may be a cluster compound containing both of a metal atom and a non-metal atom.

The hydrophobic cluster compound may be a cluster compound having another atom enclosed therein. Examples of such a cluster compound include a non-metal cluster compound having a metal atom enclosed therein; and an organometallic coordination compound such as a coordination compound of phthalocyanine and a metal atom, and a coordination compound of porphyrin and a metal atom. Preferred examples of such a coordination compound include a metallic coordination compound of ruthenium or cobalt.

The maximum diameter of the hydrophobic cluster compound to which water solubility or water dispersibility to be imparted is preferably 500 nm or less, especially preferably 200 nm or less. When complexed with a β-1,3-1,6-D-glucan having a degree of branching of 50 to 100%, such a large hydrophobic compound having a maximum diameter of 5 nm or more can be made soluble or dispersible in water.

In some cases, some primary particles of the cluster compound form larger aggregates. In this case, however, what affects the formation of a complex with a β-1,3-1,6-D-glucan is the size of the primary particles. Hence, the maximum diameter herein refers to the maximum diameter of the primary particles. When the cluster compound is in the form of a fiber such as a carbon nanotube, the circumference affects the formation of a complex of the cluster compound with a β-1,3-1,6-D-glucan. Hence, the maximum diameter herein refers to the nanotube's maximum diameter, which is closely related to its circumference. When the cluster compound is in the form of a coil such as a carbon nanocoil, the circumference affects the formation of a complex of the cluster compound with a β-1,3-1,6-D-glucan. Hence, the maximum diameter herein refers to the nanocoil's maximum diameter, which is closely related to its circumference.

Among metal cluster compounds, preferred is a cluster compound of platinum (Pt), gold (Au), silver (Ag), copper (Cu), titanium (Ti), zinc (Zn), iron (Fe), cobalt (Co), magnesium (Mg), aluminum (Al), zirconium (Zr), or an oxide thereof; more preferred is a cluster compound of platinum (Pt), gold (Au), silver (Ag), copper (Cu), titanium (Ti), zinc (Zn), or an oxide thereof.

Among the non-metal cluster compounds, preferred is a carbon cluster compound such as a fullerene, a carbon nanotube, and a carbon nanocoil, and a boron cluster compound such as a carborane; and more preferred is a compound having a regular polyhedron structure, for example, a fullerene or a carborane.

Fullerenes having about 60 to 120 carbon atoms are known, and the carbon number is, for example, 60, 70, 76, 78, 80, 82, 84, 86, 88, 90, 92, 94, or 96. The carbon number is not particularly limited in the present invention, but a fullerene having about 60 to 70 carbon atoms is preferable in that such a fullerene is readily available and is excellent in stability and water solubility when complexed with a β-1,3-1,6-D-glucan. A fullerene having a heteroatom such as scandium (Sc), lanthanum (La), cerium (Ce), titanium (Ti), and nitrogen (N) enclosed therein can also be used.

Single-walled carbon nanotubes, which usually have a diameter of about 1 nm, are preferably bundled in a group of one to several (for example, 10) in the present invention in order to achieve better solubility. The optimal diameter of the bundled carbon nanotubes is about 1 to 20 nm. The present invention also makes it possible to impart sufficient water solubility or water dispersibility to a multi-walled carbon nanotube, in which a plurality of single-walled carbon nanotubes are stacked in a nested manner. The diameter of such a multi-walled carbon nanotube is, for example, about 150 to 200 nm, and the length is, for example, about 1 to 10 μm.

Carborane is a generic term for compounds and ions having a polyhedral borane structure in which some of the boron atoms are substituted with carbon atoms. Carboranes with 6 to 12 polyhedron vertices are known, but the number of the polyhedron vertices is not particularly limited in the present invention. In particular, m-carborane and o-carborane, which are represented by $B_{10}C_2H_{12}$ and have a regular icosahedral structure, are preferable in that they are excellent in stability when complexed with a β-1,3-1,6-D-glucan.

(1-2) β-1,3-1,6-D-Glucan

The degree of branching, which is the ratio of the number of β-1,6 linkages constituting side chains to the number of β-1,3 linkages constituting the main chain, of the β-1,3-1,6-D-glucan used in the present invention is usually about 50 to 100%, preferably about 75 to 100%, more preferably about 85 to 100%.

Whether a β-1,3-1,6-D-glucan has the above degree of branching can be confirmed by the liberation of glucose and gentiobiose as decomposition products after exo-β-1,3-glucanase hydrolysis of the β-1,3-1,6-D-glucan (Kitalase M, KI Chemical Industry Co., Ltd.) or confirmed by determining the integral ratio of the NMR signals (Biseibutsu Riyo no Daitenkai (Great development of microorganisms), supervised by Tadayuki Imanaka, 1012-1015, NTS Inc. (2002)).

(a) β-1,3-1,6-D-glucan Produced by Microorganisms Belonging to the Genus of *Aureobasidium* Sp.

A β-1,3-1,6-D-glucan having the above degree of branching can be obtained from a microorganism belonging to the genus of *Aureobasidium* sp.

A β-1,3-1,6-D-glucan derived from a microorganism belonging to the genus of *Aureobasidium* sp. exhibits two signals at about 4.7 ppm and about 4.5 ppm in a $^1$H NMR spectrum obtained using a 1 N solution of sodium hydroxide in deuterium oxide as a solvent. Since it is well-known that NMR values vary with slight changes in the measuring conditions and are accompanied by error, the values "about 4.7 ppm" and "about 4.5 ppm" are to be understood as values with a fluctuation range that can usually be predicted (for example, ±0.2).

The viscosity at 30° C. and pH 5.0 of a 0.50 (w/v) aqueous solution of a β-1,3-1,6-D-glucan having the above degree of branching is preferably 200 cP (mPa·s) or less, more preferably 100 cP (mPa·s) or less, further preferably 50 cP (mPa·s) or less. Usually, the lower limit of the viscosity may be about 10 cP (mPa·s).

The viscosity in the present invention is a value measured with a BM-type rotatory viscometer.

A β-1,3-1,6-D-glucan produced by a microorganism belonging to the genus of *Aureobasidium* sp. is preferable in that it is water-soluble and that it is secreted outside the fungus cell and thus the recovery of the β-1,3-1,6-D-glucan is easier than that of a β-glucan contained in the cell wall of a mushroom or a baker's yeast. A microorganism belonging to the genus of *Aureobasidium* sp. can produce glucans having a molecular weight ranges from as low as several tens of thousands to as high as one million or more depending on the culture conditions.

Inter alia, a β-1,3-1,6-D-glucan produced by *Aureobasidium pullulans* is preferable. Especially preferred is a β-1,3-1,6-D-glucan produced by an *Aureobasidium pullulans* GM-NH-1A1 or GM-NH-1A2 strain (deposited under Accession Nos. FERM P-19285 and FERM P-19286, respectively, in International Patent Organism Depositary of the National Institute of Advanced Industrial Science and Technology). The GM-NH-1A1 and GM-NH-1A2 strains are mutants of the K-1 strain of *Aureobasidium* sp. The K-1 strain of *Aureobasidium* sp. is known to produce two types of β-1,3-1,6-D-glucans having molecular weights of two million or more and about 1 million, respectively.

It is known that a β-1,3-1,6-D-glucan produced by a microorganism belonging to the genus of *Aureobasidium* sp. usually contains a sulfur-containing group, whereas a β-glucan produced by the K-1 strain contains a sulfoacetic acid group (Arg. Biol. Chem., 47, 1167-1172 (1983); and Kagaku To Kogyo (CHEMISTRY & CHEMICAL INDUSTRY), 64, 131-135 (1990)). Therefore, β-1,3-1,6-D-glucans produced by the GM-NH-1A1 and GM-NH-1A2 strains are also considered to contain a sulfoacetic acid group. Among microorganisms belonging to the genus of *Aureobasidium* sp., there exist species and strains that produce a β-1,3-1,6-D-glucan containing a phosphorus-containing group such as a phosphate group, a malic acid group, or the like.

The GM-NH-1A1 and GM-NH-1A2 strains, as described in Example below, produce both of a high molecular weight β-glucan (microparticulate glucan) having a main peak at an apparent molecular weight of 500,000 to 2,500,000 and a low molecular weight β-glucan having a main peak at an apparent molecular weight of 20,000 to 300,000. The diameter of the primary particle of the microparticulate glucan is about 0.05 to 2 μm.

The solubility of a β-1,3-1,6-D-glucan depends on pH and temperature. When a 2 mg/mL aqueous β-1,3-1,6-D-glucan solution is prepared at pH 3.5 and 25° C., 50% by weight or more of β-1,3-1,6-D-glucan forms primary particles having a diameter of 0.05 to 2 μm and the rest thereof dissolves in water. In the present invention, the particle diameter is a value measured by laser diffraction scattering.

The viscosity of the β-1,3-1,6-D-glucan of the present invention in the form of an aqueous solution is preferably less than that of a natural β-1,3-1,6-D-glucan produced by a microorganism belonging to the genus of *Aureobasidium* sp. The viscosity of a 0.5% (w/v) aqueous solution of such a low-viscosity β-1,3-1,6-D-glucan at 30° C. and pH 5.0 is usually 200 cP (mPa·s) or less, preferably 100 cP (mPa·s) or less, more preferably 50 cP (mPa·s), further preferably 10 cP or less.

The low-viscosity glucan may have a primary structure similar to that of a natural β-1,3-1,6-D-glucan produced by a microorganism belonging to the genus of *Aureobasidium* sp. In particular, the low-viscosity glucan exhibits two signals at about 4.7 ppm and about 4.5 ppm in a $^1$H NMR spectrum obtained using a 1 N solution of sodium hydroxide in deuterium oxide as a solvent. Since it is well-known that NMR values vary with slight changes in the measuring conditions and are accompanied by error, the values "about 4.7 ppm" and "about 4.5 ppm" are to be understood as values with a fluctuation range that can usually be predicted (for example, ±0.2).

The concentration of a metal ion that may be contained in the β-1,3-1,6-D-glucan of the present invention is preferably 0.4 g or less, more preferably 0.2 g or less, further preferably 0.1 g or less, relative to 1 g of the solid β-1,3-1,6-D-glucan content. When the β-1,3-1,6-D-glucan as a raw material is in the form of an aqueous solution, the metal ion concentration is preferably 120 mg or less, more preferably 50 mg or less, further preferably 20 mg or less, per 100 mL of the aqueous solution.

Examples of the metal ion herein include alkali metal ions, alkaline earth metal ions, Group 3 to 5 metal ions, and transition metal ions. Typical examples of the metal ion that may contaminate the β-1,3-1,6-D-glucan include a potassium ion and a sodium ion that are derived from an alkali used in the production of the low-viscosity β-1,3-1,6-D-glucan. The metal ion concentration can be adjusted by ultrafiltration or dialysis.

The β-1,3-1,6-D-glucan having a metal ion concentration in the above ranges is least prone to gel, aggregate, or precipitate while stored or heat-sterilized in the form of an aqueous solution. Such a β-1,3-1,6-D-glucan in the form of a solid is, when redissolved, least prone to aggregate.

(b) Production Process for β-1,3-1,6-D-glucan by Microorganism Belonging to the Genus of *Aureobasidium* Sp.

A β-1,3-1,6-D-glucan having a degree of branching of 50 to 100% can be obtained, for example, as a precipitate by adding an organic solvent to the culture supernatant of a microorganism that produces such a β-1,3-1,6-D-glucan.

There have been reported various methods for culturing a microorganism belonging to the genus of *Aureobasidium* sp. and allowing the production of a β-1,3-1,6-D-glucan. Carbon sources that can be used for the culture medium may be, for example, carbohydrates such as sucrose, glucose, and fructose; organic nutrient sources such as peptone and a yeast extract. Nitrogen sources that can be used may be, for example, inorganic nitrogen sources such as ammonium sulfate, sodium nitrate, and potassium nitrate. In some cases, another effective way to increase the production of a β-glucan is adding, as appropriate, inorganic salts such as sodium chloride, potassium chloride, a phosphoric salt, a magnesium salt, and a calcium salt; trace mineral salts such as iron, copper, and manganese; vitamins; and/or the like.

There has been reported that a microorganism belonging to the genus of *Aureobasidium* sp. cultured in a Czapek medium containing sucrose as a carbon source and supplemented with ascorbic acid can produce a high concentration of a β-1,3-1, 6-D-glucan (Arg. Biol. Chem., 47, 1167-1172 (1983); Kagaku To Kogyo (CHEMISTRY & CHEMICAL INDUSTRY), 64, 131-135 (1990); and JP 7-51082 A). However, the medium is not particularly limited as long as it allows the microorganism to grow and produce a β-1,3-1,6-D-glucan. Organic nutrient sources such as a yeast extract and peptone may be added as needed.

The conditions for aerobic culture of a microorganism belonging to the genus of *Aureobasidium* sp. in the above medium are, for example, at a temperature of about 10 to 45° C., preferably about 20 to 35° C. and at a pH of about 3 to 7, preferably about 3.5 to 5.

For effective control of the culture pH, an alkali or acid may be used to adjust the pH of the culture solution. A defoaming agent may be added as appropriate for defoaming the culture solution. The incubation time is usually 1 to 10 days, preferably 1 to 4 days. This time period allows the production of a β-glucan. The incubation time may be determined by monitoring the production of a β-glucan.

After a microorganism belonging to the genus of *Aureobasidium* sp. is cultured with aeration and agitation in a culture solution under the above conditions for 4 to 6 days, the culture solution contains 0.1 to several percent (w/v) of a β-glucan polysaccharide whose principal component is a β-1,3-1,6-D-glucan. The culture solution has a very high viscosity, which is several hundred to several thousand cP (mPa·s) at 30° C. measured with a BM-type rotatory viscometer (TOKI SANGYO Co., Ltd.). By adding, for example, an organic solvent to the supernatant obtained by centrifuging the culture solution, the β-1,3-1,6-D-glucan can be obtained as a precipitate.

<Production Process for Low-Viscosity β-1,3-1,6-D-Glucan>

The viscosity of the culture solution containing the above high-viscosity β-1,3-1,6-D-glucan rapidly decreases as soon as an alkali is added with stirring at normal temperature.

The alkali is not particularly limited as long as it is water-soluble and can be used as a pharmaceutical or food additive. Examples of the alkali include an aqueous alkali carbonate solution such as an aqueous calcium carbonate solution, an aqueous sodium carbonate solution, an aqueous potassium carbonate solution, and an aqueous ammonium carbonate solution; an aqueous alkali hydroxide solution such as an aqueous sodium hydroxide solution, an aqueous potassium hydroxide solution, and an aqueous calcium hydroxide solution; and an aqueous ammonia solution. The alkali may be added in such an amount that it can increase the pH of the culture solution to 12 or higher, preferably 13 or higher. For example, in cases where sodium hydroxide is used to increase the pH of the culture solution, sodium hydroxide may be added so that the final concentration of sodium hydroxide is 0.5% (w/v) or more, preferably 1.25% (w/v) or more. As soon as the alkali is added to the culture solution and thoroughly stirred, the viscosity of the culture solution rapidly decreases.

After alkali treatment, insoluble substances such as the fungus cells are separated from the culture solution. Due to the decreased viscosity of the culture solution, insoluble substances can be easily separated from the glucan by various methods such as a method involving allowing the fungus cells to spontaneously precipitate and recovering the supernatant (decantation), centrifugation, dead-end filtration with a filter paper or a filter cloth, filter press, and membrane filtration (ultrafiltration with a MF membrane). In dead-end filtration with a filter paper or a filter cloth, use of a filter aid such as cerite is one option. Among the above methods, filter press is industrially preferable for the removal of the fungus cells. If needed, prior to the removal of insoluble substances, the β-D-glucan solution may be diluted with water. Too high concentration makes it difficult to remove insoluble substances, and too low concentration makes it inefficient. The concentration of the β-D-glucan is preferably about 0.1 to 20 mg/mL, more preferably about 0.5 to 10 mg/mL, further preferably about 1 to 5 mg/mL.

Next, an acid is added to neutralize the glucan-containing solution. Neutralization may be performed prior to the removal of insoluble substances. The acid is not particularly limited as long as it can be used as a pharmaceutical or food additive. Examples of the acid include hydrochloric acid, phosphoric acid, sulfuric acid, citric acid, and malic acid. The acid is added in such an amount that it can adjust the pH of the solution or the culture solution to neutral (about pH 5 to 8). In other words, adjusting the pH to 7 is not necessarily required.

The viscosity at 30° C. and pH 5.0 of a 0.5% (w/v) solution of the β-1,3-1,6-D-glucan that has been subjected to alkali treatment (pH 12 or higher) followed by neutralization is usually 200 cP or less, in some cases, 100 cP or less, 50 cP or less, or 10 cP or less. The viscosity varies depending on the production or purification process.

The viscosity of the alkali-treated low-viscosity β-1,3-1,6-D-glucan will never be increased even when subjected to neutralization. Further, at normal temperature (15 to 35° C.), the viscosity will never be increased even when the glucan solution is acidified to below pH 4.

Instead of performing the removal of the fungus cells and the like from the culture supernatant after alkali treatment and neutralization, the removal can be performed prior to alkali treatment and neutralization.

Soluble contaminants having a lower molecular weight than the glucan (for example, a salt or the like) can be removed from the obtained aqueous glucan solution by, for example, ultrafiltration.

After the alkali treatment and the removal of the fungus cells, ultrafiltration can be performed under the alkaline condition without neutralization. The thus-obtained purified β-1,3-1,6-D-glucan is further excellent in transparency, heat stability, and prolonged storage stability. The alkaline condition is pH 10 or higher, preferably pH 12 or higher, and the upper limit of the pH is usually about 13.5.

The β-1,3-1,6-D-glucan contained in the aqueous solution thus obtained can be once precipitated from the aqueous solution in both cases where the glucan is to be dried and used for a solid preparation and where the glucan is to be used for a liquid preparation. The precipitation method of the β-1,3-1,6-D-glucan is not particularly limited. For example, the β-1,3-1,6-D-glucan can be precipitated by concentrating the aqueous glucan solution through ultrafiltration so that the concentration of the glucan solution is 1% w/w or more, and adding an alcohol such as ethanol in a volume equivalent to that of the aqueous glucan solution or in a larger volume, preferably in a 2-fold volume or more. When addition of ethanol is performed after the pH of the glucan solution is adjusted to acidity, preferably below pH 4, more preferably pH 3 to 3.7, with the use of an organic acid such as citric acid, a highly purified β-1,3-1,6-glucan powder can be obtained.

In addition, since such a low-viscosity β-1,3-1,6-D-glucan solution can be easily concentrated through ultrafiltration, the amount of the alcohol used for alcohol precipitation can be reduced.

For obtaining the glucan in a solid state, the aqueous solution of the low-viscosity β-1,3-1,6-D-glucan may be directly dried, or alternatively, the β-1,3-1,6-D-glucan may be once precipitated from the solution and then dried. Drying can be performed by a known method such as spray drying and lyophilization.

(1-3) Ratio of Hydrophobic Cluster Compound and β-1,3-1,6-D-Glucan

The ratio of the hydrophobic cluster compound and the β-1,3-1,6-D-glucan in the complex is, by dry weight, preferably about 1:0.01 to 1000 (hydrophobic cluster compound:β-1,3-1,6-D-glucan), more preferably about 1:0.1 to 100, further preferably about 1:0.1 to 50, especially preferably about 1:0.1 to 20. The complex having the above ratio has sufficient water solubility.

(2) Production Process for Complex (2-1) High Speed Vibration Milling Method

The production process for the complex of the present invention described above is not particularly limited.

The complex can be produced by, for example, a process comprising the steps of agitating the hydrophobic cluster compound with a β-1,3-1,6-D-glucan having a degree of branching (a ratio of β-1,6 linkages to β-1,3 linkages) of 50 to 100% while maintaining the solid state, and agitating the mixture with added water.

The mixing ratio of the hydrophobic cluster compound and the β-1,3-1,6-D-glucan is, by dry weight, preferably about 1:0.01 to 1000 (hydrophobic cluster compound:β-1,3-1,6-D-glucan), more preferably about 1:0.1 to 100, further preferably about 1:0.1 to 50, especially preferably about 1:0.1 to 20.

The mixing of the hydrophobic cluster compound and the β-1,3-1,6-D-glucan while maintaining the solid state may be performed by any method as long as the compound and the glucan are sufficiently milled and mixed. The mixing may be performed using various kinds of conventional milling and mixing apparatus. Examples of the mixing method include a milling and mixing method using a planetary ball mill or a centrifugal ball mill; and a high speed vibration milling method using a high speed vibration mill, in which materials to be mixed are placed with a hard ball in a container and the container is vibrated at high speed.

Preferred is a high speed vibration milling method. The vibration frequency may be, for example, about 10 to 120 s$^{-1}$ (about 10 to 120 Hz).

The vibration time may be, for example, about 5 to 60 minutes. The amplitude is, for example, when the hollow part of the container has a bottom diameter of 12 mm and a longitudinal length of 50 mm, is usually about 5 to 100 mm. The amplitude herein refers to the distance from the vibration center to the maximum displacement point, in which the container is fully displaced. The diameter of the hard ball may be about 2 to 10 mm when the bottom diameter of the hollow part of the container is 12 mm and the longitudinal length of the hollow part is 50 mm. The material of the hard ball is, for example, agate, stainless steel, alumina, zirconia, tungsten carbide, chromium steel, Teflon (registered trademark), or the like. The number of the hard ball placed in the container may be about 1 to 6.

Agitation of the raw materials in the solid state can be performed at room temperature.

To the thus obtained mixture of the hydrophobic cluster compound and the β-1,3-1,6-D-glucan, water is added and stirred together. The water may contain a buffer agent, a salt, or the like in such an amount that the buffer agent, the salt, or the like does not prevent the formation of the complex. The amount of the water may be about 10 to 10,000 parts by weight relative to 1 part by weight of the mixture. The stirring in this step can be performed using, for example, a magnetic stirrer. The stirring step is preferably performed at room temperature for at least two days, for example, 4 to 7 days.

In this way, a solution containing a dissolved complex of the hydrophobic cluster compound and the β-1,3-1,6-D-glucan can be obtained. Water-insoluble contaminants may be removed as needed by centrifugation at about 1,000 to 20,000 g for about 5 to 60 minutes.

(2-2) Process for Mixing in Polar Solvent and Ripening

The complex of the present invention described above can also be produced by a process comprising the steps of mixing, in a polar solvent, the hydrophobic cluster compound and a β-1,3-1,6-D-glucan having a degree of branching (a ratio of β-1,6 linkages to β-1,3 linkages) of 50 to 100%, and adding water to the obtained mixture and allowing the mixture to ripen.

The ratio of the hydrophobic cluster compound and the β-1,3-1,6-D-glucan is, by dry weight, preferably about 1:0.01 to 1000 (hydrophobic cluster compound:β-1,3-1,6-D-glucan), more preferably about 1:0.1 to 100, further preferably about 1:0.1 to 50, especially preferably about 1:0.1 to 20.

The amount of the polar solvent may be about 10 to 10,000 parts by weight relative to 1 part by weight of the β-1,3-1,6-D-glucan.

The polar solvent may be a protonic polar solvent such as water, acetic acid, formic acid, and a lower alcohol; or a non-protonic polar solvent such as dimethylsulfoxide, acetone, acetonitrile, N,N-dimethylformamide, methylene chloride, and tetrahydrofuran. Among these, preferred is a non-protonic polar solvent and more preferred is dimethylsulfoxide.

The hydrophobic cluster compound and the β-1,3-1,6-D-glucan may be simultaneously mixed with the polar solvent; alternatively, either one may be mixed with the polar solvent in advance, the other is added thereto, and the mixture is mixed.

The mixing can be performed using, for example, a magnetic stirrer.

Next, water is added, preferably in an amount of about 1 to 15 parts by weight relative to 1 part by weight of the mixture, and usually the mixture is allowed to stand at room temperature for 1 to 3 days for ripening. The water may contain a buffer agent, a salt, or the like in such an amount that the buffer agent, the salt, or the like does not prevent the formation of the complex.

In this way, a solution containing a dissolved complex of the hydrophobic cluster compound and the β-1,3-1,6-D-glucan can be obtained. Water-insoluble contaminants may be removed as needed by centrifugation at about 1,000 to 20,000 g for about 5 to 60 minutes.

The obtained solution is usually dialyzed against 50- to 500-fold volume of distilled water (MWCO=3,500) to remove the polar solvent. The dialyzed solution is recovered and concentrated with an evaporator or the like. In this way, an aqueous solution containing the dissolved complex of the hydrophobic cluster compound and the β-1,3-1,6-D-glucan can be obtained.

(3) Others

The above production process for the complex of the present invention is also to be understood as a process for making a hydrophobic cluster compound soluble or dispersible in water or a process for imparting water solubility or water dispersibility to a hydrophobic cluster compound.

The complex of the present invention is safe and thus applicable as a medicine.

The complex of the hydrophobic cluster compound of the present invention can be applied to various materials such as catalyst materials, magnetic recording materials, conductive film forming materials, semiconductor film forming materials, and pigments. For example, a coating can be formed by applying, to a substrate, a complex of a metal cluster compound or a carbon nanotube of the present invention, and drying and calcining the applied complex at 20 to 600° C. The substrate may be any heat-resistant substrate that does not burn out or deteriorate during drying and calcination and is generally used to constitute an electrode, wiring, a circuit, or the like. Examples of the substrate include a metal substrate such as iron, copper, and aluminum; a heat-resistant resin substrate such as a polyimide film; and a glass substrate. The application method may be a known method. Examples of the application method include screen printing, dip coating, spraying, and spin coating. In addition, by using an ink jet head, it is also possible to apply the complex only to the part in need of application. After applied, the complex can be dried and calcined at about 20 to 600° C., preferably about 100 to 450° C., further preferably about 100 to 350° C. The calcination atmosphere is preferably an inert gas atmosphere or a reducing atmosphere. The calcination time is about 0.1 to 3 hours, preferably about 0.2 to 2 hours. The resulting coating can serve as wiring.

Further, with the addition of a cross-linking agent, the complex of the hydrophobic cluster compound of the present invention can be molded into a shaped product. Examples of the cross-linking agent include a long-chain polysaccharide such as curdlan; an acid anhydride; and an isocyanate compound.

The shaped product made from the complex of the hydrophobic cluster compound of the present invention can be used for various applications such as various sensors, radiators, magnetic bodies, solid catalysts, optical elements, and conductors.

EXAMPLES

The present invention will be described in more detail below with reference to Examples, but the present invention is not limited thereto.

Experimental Example

Production of Purified β-1,3-1,6-D-Glucan (1) Preparation of Low-Viscosity β-1,3-1,6-D-Glucan
(1-1) Production of β-Glucan by Culturing In a 500 mL Sakaguchi flask was placed 100 mL of a liquid medium having the composition shown in Table 1 below, and the medium was autoclaved at 121° C. for 15 minutes. One platinum loop of an *Aureobasidium pullulans* GM-NH-1A1 strain (FERM P-19285) from a slant having the same medium composition was aseptically inoculated into the liquid medium, and cultured at 30° C. with aeration and agitation at 130 rpm for 24 hours to prepare a strain culture solution.

Next, 200 L of a medium having the same medium composition was placed in a 300 L culture apparatus (B.E. MARUBISHI Co., Ltd.) and autoclaved at 121° C. for 15 minutes. Into this medium, 2 L of the above strain culture solution was aseptically inoculated and cultured at 27° C. with aeration at 40 L/min and agitation at 200 rpm. The pH of the medium was adjusted within the range of 4.2 to 4.5 using sodium hydroxide and hydrochloric acid. The turbidity due to the fungus cells 96 hours later was 23 OD at 660 nm, the polysaccharide concentration was 0.5% (w/v), and the substituted sulfoacetic acid content calculated from the sulfur content was 0.09%.

<Polysaccharide Concentration Measurement>

The polysaccharide concentration was determined as follows. Several mL of the above culture solution was taken out and the fungus cells in the culture solution were removed by centrifugation. Ethanol in such an amount that the final concentration would be 66% (v/v) was added to the supernatant to precipitate polysaccharides. The precipitate was recovered and dissolved in deionized water. The polysaccharides in the precipitate were quantified by a phenol-sulfuric acid method.

<Substituted Sulfa Content Measurement>

To a culture supernatant obtained in the same manner as described above, was added ethanol in such an amount that the final concentration would be 66%, and the precipitated β-glucan was recovered. Next, the β-glucan was redissolved in deionized water and centrifuged. To the supernatant was added sodium chloride in such an amount that the final concentration would be 0.9% and the β-glucan was again recovered with 66% ethanol. This procedure for recovery and purification of the β-glucan was further repeated twice. The obtained aqueous β-glucan solution was dialyzed against deionized water and lyophilized to give a β-glucan powder.

Composition analysis of the β-glucan powder was carried out by combustion tube method, which involves powder burning, absorption, and ion chromatography. The S content was 239 mg/kg, and the substituted sulfoacetic acid content calculated from the S content was 0.09%.

TABLE 1

| Component | Concentration (%(w/v)) |
|---|---|
| Sodium nitrate | 0.2 |
| Dipotassium phosphate | 0.1 |
| Potassium chloride | 0.05 |
| Magnesium sulfate heptahydrate | 0.05 |
| Ferrous sulfate heptahydrate | 0.001 |
| Ascorbic acid | 0.6 |
| Sucrose | 3.3 |
| Add water to the calibration mark | |

(1-2) Alkali Treatment

The viscosity of the culture solution thus obtained was measured with a BM-type rotatory viscometer (TOKYO KEIKI INC.) at 30° C. at 12 rpm and determined to be 1500 cP (mPa·s). The rotor for the measurement was selected as appropriate according to the viscosity.

As soon as 25% (w/w) sodium hydroxide was added to the culture solution in such an amount that the final concentration of sodium hydroxide would be 2.4% (w/v) and the mixture was thoroughly stirred (at pH 13.6), the viscosity rapidly decreased. Next, the solution was neutralized with a 50% (w/v) aqueous citric acid solution so that the pH was 5.0, and the viscosity at a concentration of 0.5% (w/v) was measured. The viscosity (at 30° C.) was determined to be 20 cP (mPa·s).

Next, 1% wt of KC FLOCK (Nippon Paper Chemicals Co., Ltd.) as a filter aid was added to the culture solution, and the fungus cells were removed with a Yabuta filter press (Yabuta Kikai Co., Ltd.) to give a culture filtrate (about 230 L). The polysaccharide concentration was 0.5% (w/v) and therefore the recovery rate was almost 100%.

(1-3) Desalination of Aqueous β-Glucan Solution

The above aqueous β-glucan solution (culture filtrate) was diluted to 0.3%, and desalinated with an ultrafiltration (UF) membrane (molecular weight cut-off: 50,000, NITTO DENKO CORPORATION). After the sodium ion concentration was reduced to 20 mg/100 mL, the pH was adjusted to 3.5 using a 50% (w/v) aqueous citric acid solution.

Next, sterilization treatment was performed by maintaining 95° C. for 3 minutes with a heating unit for hot packing (Hisaka Works, Ltd.) to give a final product, an aqueous β-glucan solution. The β-glucan concentration of this solution measured by a phenol-sulfuric acid method was 0.22% (w/v). The total yield from the culture solution was about 73%.

<Measurement of Sulfur Content>

The obtained aqueous β-glucan solution was dialyzed against deionized water and lyophilized to give a β-glucan powder. The composition analysis of this β-glucan revealed that the S content was 330 mg/kg and the substituted sulfoacetic acid content calculated from the S content was 0.12%.

<Determination of Linking State>

The above desalinated culture filtrate was subjected to a Congo-red method and the wavelength shift from about 480 nm to about 525 nm was observed, which proved that the culture filtrate contained a glucan containing β-1,3 linkages (K. Ogawa, Carbohydrate Research, 67, 527-535 (1978); and Biseibutsu Riyo no Daitenkai (Great development of microorganisms), supervised by Tadayuki Imanaka, 1012-1015, NTS Inc. (2002)). The shift of the maximum value was Δ0.48/500 μg of polysaccharides.

An amount of 15 mL of the above culture filtrate was taken out, and 30 mL of ethanol was added thereto. The mixture was centrifuged at 4° C. at 1000 rpm for 10 minutes, and the precipitated polysaccharides were recovered. The precipitate was washed with 66% ethanol and centrifuged at 4° C. at 1000 rpm for 10 minutes. After 2 mL of deionized water and 1 mL of a 1 N aqueous sodium hydroxide solution were added to the precipitated polysaccharides and the mixture was stirred, the mixture was kept at 60° C. for 1 hour to dissolve the precipitate. After frozen at −80° C., the mixture was lyophilized overnight. The dried powder was dissolved in 1 mL of a 1 N solution of sodium hydroxide in deuterium oxide and subjected to two-dimensional NMR.

A $^1$H NMR spectrum that correlates with two-dimensional NMR ($^{13}$C-$^1$H COSY NMR) at 106 ppm is shown in FIG. 1. In this spectrum, two signals were observed at about 4.7 ppm and about 4.5 ppm.

The results proved that the β-glucan was a β-1,3-1,6-D-glucan (Biseibutsu Riyo no Daitenkai (Great development of microorganisms), supervised by Tadayuki Imanaka, 1012-1015, NTS Inc. (2002)). From the integral ratio of each $^1$H NMR signal, it was revealed that β-1,3 linkages/β-1,6 linkages was 1.15. Thus the degree of branching (the ratio of β-1,6 linkages constituting side chains to β-1,3 linkages constituting the main chain) is about 87%.

<Determination of Particle Size>

Figure 2:
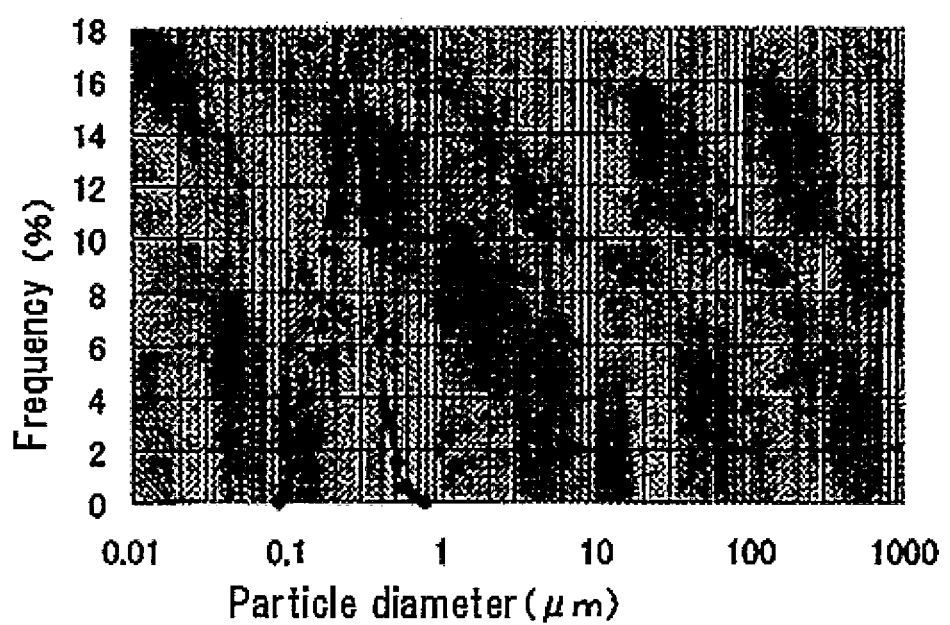
FIG. 2 is a graph showing the particle size distribution in an ultrasonicated culture solution containing the *Aureobasidium pullulans*-derived glucan obtained in Example below.

The particle size in the culture solution was measured with a laser diffraction/scattering particle size distribution analyzer (LA-920, HORIBA, Ltd.). Particle-size peaks were observed at about 0.3 μm and about 100 μm. Next, particle size measurement was performed under ultrasonic irradiation. The 100 μm peak instantly disappeared and the 0.3 μm peak intensified, and only the 0.3 μm peak eventually remained. The particle size distribution in the culture solution under ultrasonic irradiation is shown in FIG. 2.

The 0.3 μm peak seems to be attributed to the primary particles of the β-1,3-1,6-D-glucan and the 100 to 200 μm peak seems to be attributed to the secondary particles, which are the aggregates of the primary particles of the β-1,3-1,6-D-glucan.

It was also observed that, upon stirring with a magnetic stirrer or gentle shaking, the secondary particles easily broke into primary particles and disappeared in the same manner as when ultrasonic irradiation was performed. Hence, the secondary particles seem to be very loose aggregations (a loosely aggregated state).

<Determination of Molecular Weight>

The solution containing the dissolved β-1,3-1,6-D-glucan and the primary particles of the β-1,3-1,6-D-glucan were subjected to molecular weight determination by gel filtration chromatography with TOYOPEARL HW-65 (TOSOH CORPORATION) (column size: 75 cm×1 cm (i.d.), molecular weight exclusion limit: 2,500,000 (dextran)) and a 0.1 M aqueous sodium hydroxide solution as an eluent. There were detected two fractions, i.e., a low molecular weight fraction with a peak of 20,000 to 300,000 derived from the dissolved β-1,3-1,6-D-glucan; and a high molecular weight fraction with an apparent molecular weight of 500,000 to 2,500,000 derived from the primary particles. The molecular weight marker was Shodex Pullulan (SHOWA DENKO K.K.).

For the purpose of separating the dissolved β-1,3-1,6-D-glucan and the microparticles, the β-1,3-1,6-D-glucan solution containing the dissolved fraction and the microparticulate fraction was filtrated through a filter (0.2 μm) (Advantech Co., Ltd.). By this filtration, the high molecular weight fraction with a molecular weight of 500,000 to 2,500,000 disappeared. The results revealed that the high molecular weight fraction contained the primary particles of the β-1,3-1,6-D-glucan and/or the secondary particles, which are the aggregates of the primary particles. Thus the molecular weight of the dissolved β-1,3-1,6-D-glucan seems to be 20,000 to 300,000.

(2) Preparation of Powdered β-Glucan

To the aqueous β-1,3-1,6-D-glucan solution containing the β-1,3-1,6-D-glucan microparticles prepared by the alkali treatment and the fungus cell removal treatment in (1-2), ethanol was added in such an amount that the final concentration would be 66% (v/v) to precipitate a polysaccharide glucan, and the precipitate was recovered by centrifugation. Next, ethanol and water were removed by lyophilization to give a dried β-1,3-1,6-D-glucan. Comparison with the total sugar concentration before the ethanol precipitation revealed that the yield was 95% or more.

Next, the obtained dried β-1,3-1,6-D-glucan was dissolved and dispersed in water in such an amount that the final concentration would be 0.3% (w/v). The molecular weight of the glucan was measured by gel chromatography with TOYOPEARL HW-65 (TOSOH CORPORATION) (column size: 75 cm×1 cm (i.d.), molecular weight exclusion limit: 2,500,000 (dextran)) and a 0.1 M aqueous sodium hydroxide solution as an eluent, in the same manner as described above. There obtained two fractions, i.e., a low molecular weight fraction with a peak of 20,000 to 300,000 and a high molecular weight fraction with an apparent molecular weight of 500,000 to 2,500,000, and therefore it was revealed that the polysaccharide consisted of two kinds of fractions having different molecular weights. The molecular weight marker was Shodex Pullulan (SHOWA DENKO K.K.).

For the purpose of separating the dissolved β1,3-1,6-D-glucan and the microparticles, the aqueous β-1,3-1,6-D-glucan solution (containing the solubilized glucan and the microparticles) prepared by the process of the present invention was filtrated through a filter (0.2 μm) (Advantech Co., Ltd.). By this filtration, the high molecular weight fraction with a molecular weight of 500,000 to 2,500,000 disappeared. The results proved that even when the β-1,3-1,6-D-glucan obtained by the process of the present invention is once dried, the dried glucan, when redissolved, exhibits the same physical behavior as that of the β-1,3-1,6-D-glucan before drying.

(3) Production of Highly Purified β-1,3-1,6-D-Glucan Powder

An amount of 90 L of the culture solution whose viscosity was lowered by alkali treatment in (1) (polysaccharide concentration: 0.5% (5 mg/mL)) was neutralized with 9 kg of a 50% aqueous citric acid solution. Next, the solution was filtered through a Yabuta filter press 40D-4 precoated with 1.8 kg of a filter aid (KC FLOCK (powdered cellulose), Nippon Paper Chemicals Co., Ltd.) for removal of the fungus cells. The filtrate was concentrated to 9 L with a spiral-wound ultrafiltration element (NTU3150-S4, NITTO DENKO CORPORATION). With stirring, the pH of the concentrated liquid was adjusted to 3.0 to 3.5 using citric acid and 18 L of ethanol was added to give a glucan/ethanol/water slurry. The viscosity of the slurry measured with a BM-type viscometer was 22 mPa·s (30° C.). The slurry was allowed to stand at room temperature for 3 hours and about 17 L of the supernatant (ethanol/water) was removed. The viscosity of the remained slurry was 45 mPa·s (30° C.). An amount of 10 L of the concentrated slurry was spray dried with a Sakamoto Giken spray dryer R-3 to give 360 g of a β-1,3-1,6-D-glucan powder (80% recovery). The purity of the obtained β-1,3-1,6-D-glucan determined by NMR spectrum analysis was 90% or more.

The obtained β-1,3-1,6-D-glucan powder was dissolved in a 1 N solution of sodium hydroxide in deuterium oxide and the NMR spectrum was measured. In this spectrum, two signals were observed at about 4.7 ppm and about 4.5 ppm. The viscosity of a 0.5% (w/v) aqueous solution of the obtained β-1,3-1,6-D-glucan powder was 200 cP or less (pH 5.0, 30° C.). The purified β-glucan obtained by the above process was used for the following tests.

Example 1 and Comparative Examples 1 to 3

Water Solubilization of Fullerene by High Speed Vibration Milling

An amount of 1 mg of a fullerene (C60 or C70) (Frontier Carbon Corporation) was mixed with 10 mg of the β-1,3-1,6-D-glucan powder (AQUA β, DAISO Co., Ltd.) obtained in the above Example, sizof Iran (Mitsui Sugar Co., Ltd.), dextran (Wako Pure Chemical Industries, Ltd.), or amylose (Wako Pure Chemical Industries, Ltd.). The mixture was placed with an agate milling ball in an agate milling jar, and high speed milling was performed with a mixer mill (MM200, Retsch Co., Ltd.) at 25 Hz for 25 minutes.

Next, 8,000 parts by weight of water was added to 1 part by weight of the mixture, and the mixture was stirred with a magnetic stirrer at room temperature for two days and dispersed by ultrasonication for 60 minutes. Centrifugation was performed at 1,400 rpm for 20 minutes to remove insoluble contaminants, and the supernatant was taken out and used as an aqueous fullerene solution.

The absorption spectrum of the aqueous fullerene solution was measured, and with the use of molar absorption coefficients at 450 nm ($E=1.3 \times 10^{-4}$) and at 381 nm ($\epsilon=3.8 \times 10^{-4}$) for C60 and C70, respectively, the fullerene concentration was calculated. The results are shown in Table 2 below.

TABLE 2

|  |  | Fullerene Concentration (mM) | |
| --- | --- | --- | --- |
|  |  | C60 | C70 |
| Example 1 | AQUA β | 250 | 120 |
| Comparative Example 1 | Sizofiran | 220 | 88 |
| Comparative Example 2 | Dextran | 200 | 50 |
| Comparative Example 3 | Amylose | 170 | 39 |

In either case of C60 or C70, the β-1,3-1,6-D-glucan having a degree of branching of 87% (AQUA β) gave a higher concentration of an aqueous fullerene solution than the β-1,3-1,6-D-glucan having a degree of branching of 33% (sizofuran). The results revealed that water-solubilization of the fullerene was efficiently achieved when the fullerene was complexed with a β-1,3-1,6-D-glucan having a degree of branching of 50% or more.

The above degree of branching of sizofuran is the value described in K. Tabata et al., Carbohydrate Research, 89, 121-135 (1981).

Example 2 and Comparative Example 4

Water Solubilization of Fullerene by DMSO-Renature Method

An aqueous solution of a γ-CD-[60] fullerene (C60) coordination compound and an aqueous solution of a γ-CD-[70] fullerene (C70) coordination compound were prepared by the method described in K. Komatsu, K. Fujiwara, Y. Murata, T. Braun, J. Chem. Soc., Perkin Trans. 1 1999, 2963.

The measurement results of the UV-Vis absorption spectra of the aqueous solution of the γ-CD-[60] fullerene (C60) coordination compound (γ-CD: Wako Pure Chemical Industries, Ltd., C60: MER Corporation) are indicated by "γ-CD-$C_{60}$" in FIGS. 3 (A) and 3 (B). The measurement results of the UV-Vis absorption spectra of the aqueous solution of the γ-CD-[70] fullerene (C70) coordination compound (γ-CD: Wako Pure Chemical Industries, Ltd., C70: MTR Ltd.) are indicated by "γ-CD-$C_{70}$" in FIGS. 4 (A) and 4 (B).

Figure 3:
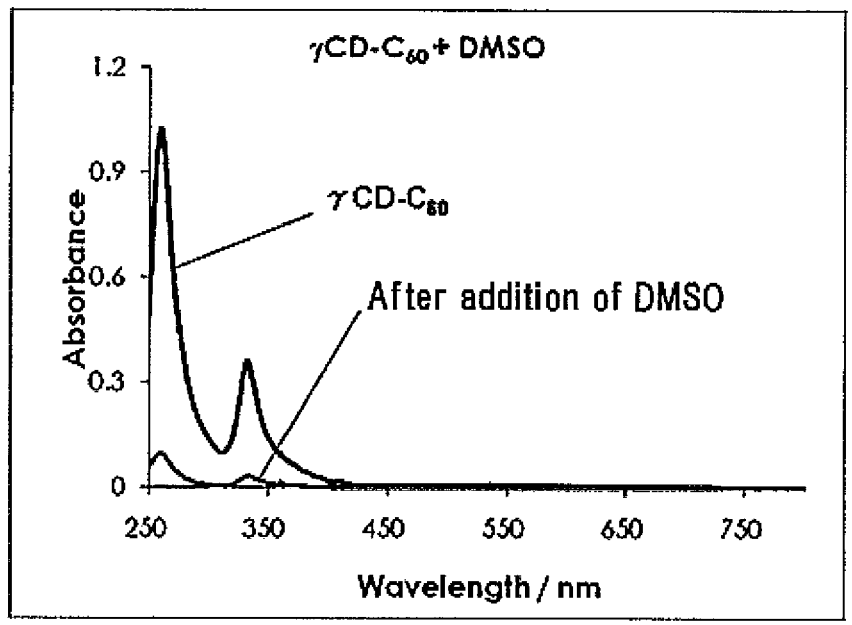
FIG. 3 (A) is a UV-Vis-NIR spectrum of an aqueous γ-CD-fullerene (C60) complex solution.
Figure 3:
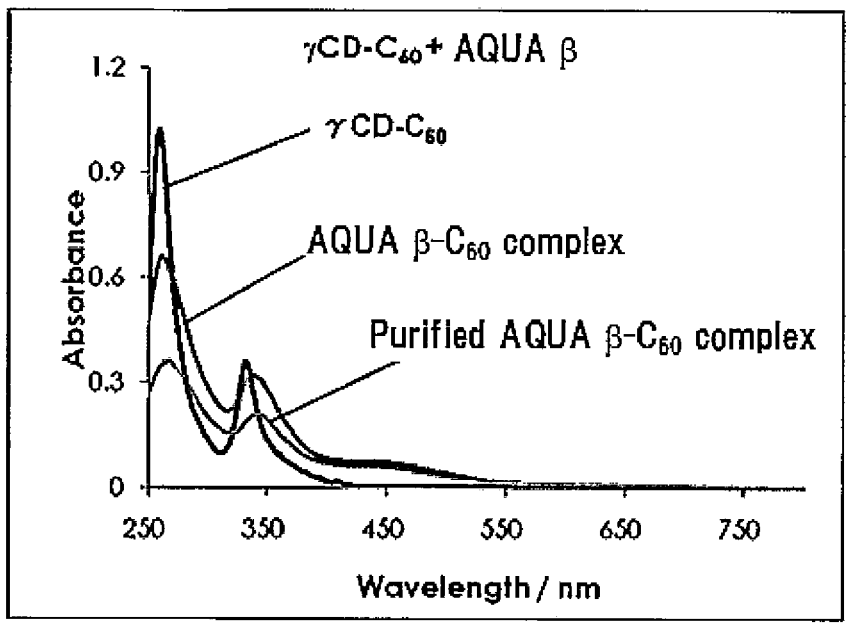
Figure 4:
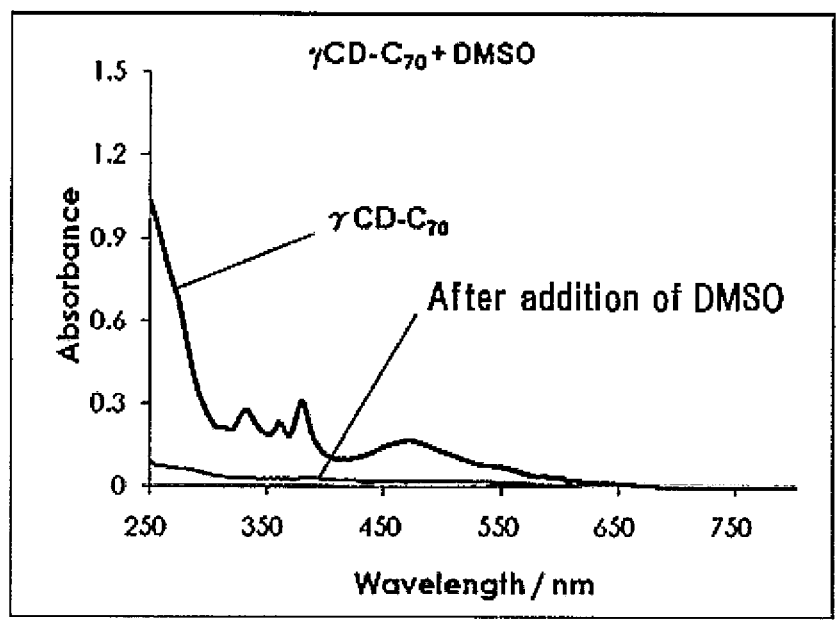
FIG. 4 (A) is a UV-Vis-NIR spectrum of an aqueous γ-CD-fullerene (C70) complex solution.
Figure 4:
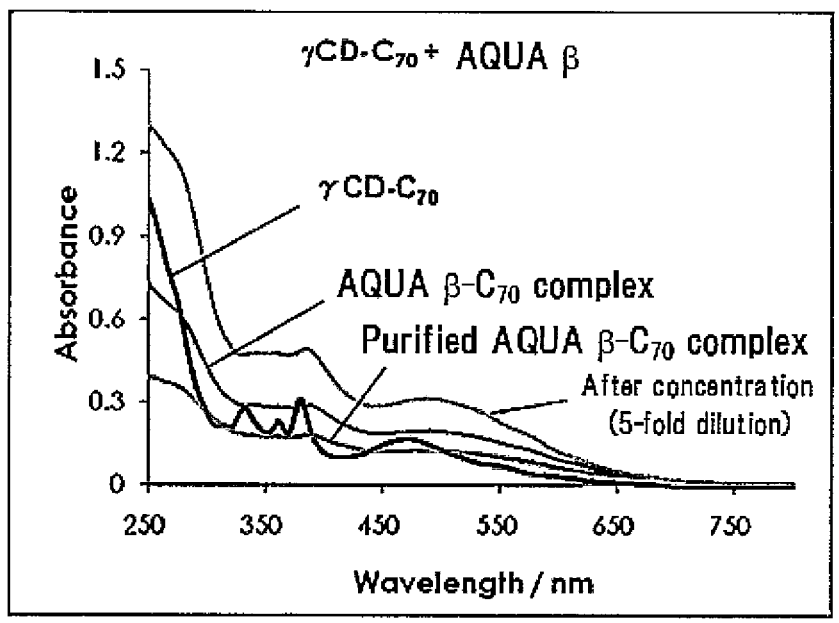

An amount of 0.5 mL of a 0.5 mM aqueous solution of the γ-CD-fullerene (C60 or C70) coordination compound was mixed with 0.5 mL of DMSO, and the obtained aqueous solution was centrifuged at room temperature at 10,000 g for 10 minutes. The measurement result of the UV-Vis absorption spectrum of the obtained supernatant is indicated by "After DMSO Addition" in FIGS. 3 (A) (C60) and 4 (A) (C70). FIGS. 3 (A) and 4 (A) show that the γ-CD-fullerene (C60 or C70) coordination compound in the aqueous solution was degraded after the addition of the DMSO solution.

An amount of 0.5 mL of a 0.5 mM aqueous solution of the γ-CD-fullerene (C60 or C70) coordination compound (γ-CD: Wako Pure Chemical Industries, Ltd., C60: MER Corporation, C70: MTR Ltd.) was mixed with 0.5 mL of an AQUA β-DMSO solution obtained by dissolving 3.24 mg of AQUA β (DAISO Co., Ltd.) in 1 mL of DMSO. The thus obtained aqueous AQUA β-fullerene (AQUA β-C60 or AQUA β-C70) complex solution was centrifuged at 10,000 g and room temperature for 10 minutes. The supernatant was recovered and the UV-Vis absorption spectrum of the aqueous complex solution was measured. The spectrum of the AQUA β-fullerene complex (C60) is indicated by "AQUA β-$C_{60}$ complex" in FIG. 3 (B), and the spectrum of the AQUA β-fullerene complex (C70) is indicated by "AQUA β-$C_{70}$ complex" in FIG. 4 (B).

Further, 0.5 mL of the obtained aqueous AQUA β-fullerene (AQUA β-C60 or AQUA β-C70) complex solution was centrifuged at 18,000 g for 1 hour to precipitate the AQUA β-fullerene complex, and the precipitate was resuspended in 0.5 mL of $D_2O$. By repeating this procedure twice, the AQUA β-fullerene (AQUA β-C60 or AQUA β-C70) complex was purified. The measurement result of the UV-Vis absorption spectrum of the purified AQUA β-C60 complex is indicated by "Purified AQUA β-$C_{60}$ complex" in FIG. 3 (B), and the measurement result of the UV-Vis absorption spectrum of the purified AQUA β-C70 complex is indicated by "Purified AQUA β-$C_{70}$ complex" in FIG. 4 (B). $^1$H NMR confirmed no existence of γ-CD in the purified aqueous solution, which indicates that γ-CD did not contribute to the water solubilization of the fullerene (C60 or C70). The line of "Purified AQUA β-$C_{60}$ Complex" in FIG. 3 (B) and the line of "Purified AQUA β-$C_{70}$ Complex" in FIG. 4 (B) indicate that AQUA β contributed to the water solubilization of the fullerene.

The concentration of the purified AQUA β-fullerene complex can be increased by reducing the amount of the solution for the resuspension during the purification process, and in this way a high-concentration aqueous solution can be obtained. For example, 0.5 mL of the aqueous AQUA β-C70 complex solution was centrifuged at 18,000 g for 1 hour to precipitate the AQUA β-C70 complex, and the obtained precipitate was resuspended in 0.05 mL of $D_2O$ to give an aqueous solution having a C70 concentration of about 0.5 mM. The measurement result of the UV-Vis absorption spectrum of a 5-fold dilution of the concentrated aqueous AQUA β-C70 complex solution is indicated by "After concentration (5-fold dilution)" in FIG. 4 (B).

The C70 concentration in the above solution was determined as follows. An excessive amount of ethanol was added to the aqueous AQUA β-C70 complex solution and the water was removed by drying under reducing pressure. The residue was redispersed in toluene for measurement of a UV-Vis absorption spectrum ($\epsilon 382=40918 \text{ cm}^{-1} \text{ mol}^{-1} \text{ dm}^3$).

As shown in FIGS. 3 (B) and 4 (B), the UV-Vis absorption spectrum of the supernatant after centrifugation of the aqueous AQUA β-fullerene complex solution obtained by mixing the AQUA β-DMSO solution and the aqueous γ-CD-fullerene coordination compound solution confirmed that the AQUA β-fullerene (C60 or C70) complex was dissolved in the aqueous solution. On the other hand, as shown in FIGS. 3 (A) and 4 (A), the absorption spectrum of the γ-CD-fullerene solution to which the DMSO solution was added suggested that the γ-CD-fullerene coordination compound was degraded. After the aqueous complex solution was centrifuged at 10,000 g for 10 minutes, almost all the fullerene precipitated.

Example 3

Evaluation of Tumor Growth Inhibition by AQUA β-Fullerene (C70) Complex in Tumor Bearing Mice (Application to Photochemotherapy)

(1) Preparation of Tumor Bearing Mice
Colon 26 cells ($60 \times 10^4$ cells/100 μL) suspended in a Hanks solution were subcutaneously administered using a 26 G injection needle to the back of 6-weeks old nude mice (BALB/c Sic-nu/nu mice, male, 18 to 23 g, Japan SLC, Inc.) under inhalation anesthesia with isoflurane.
(2) Evaluation of Anti-Tumor Effect of AQUA β-Fullerene (C70) Complex
The tumor bearing mice obtained as described above were divided into two groups, each consisting of five mice. To one group, the AQUA β-fullerene (C70) complex was administered and light irradiation was performed. To the other group, only light irradiation was performed. The AQUA β-fullerene (C70) complex was administered as follows: 400 μl of an aqueous AQUA β-fullerene (C70) complex solution having a fullerene concentration of $9.33 \times 10^{-5}$ (M) was mixed with 100 μl of a 25% glucose solution, the mixture was adjusted to isotonicity, and 100 μl of the solution was locally injected using a 30G injection needle to the tumor of the mice. A 30-minute light irradiation one hour after the administration was performed on the first day of the administration, three days later, five days later, and seven days later, in total four times. The light irradiation was performed by irradiating the tumor with a Xe lamp at a height of 5 cm from the tumor for 30 minutes one hour after the administration of the aqueous AQUA β-fullerene (C70) complex solution. Irradiation intensity was set at 35 mW/cm$^2$.

Figure 5:
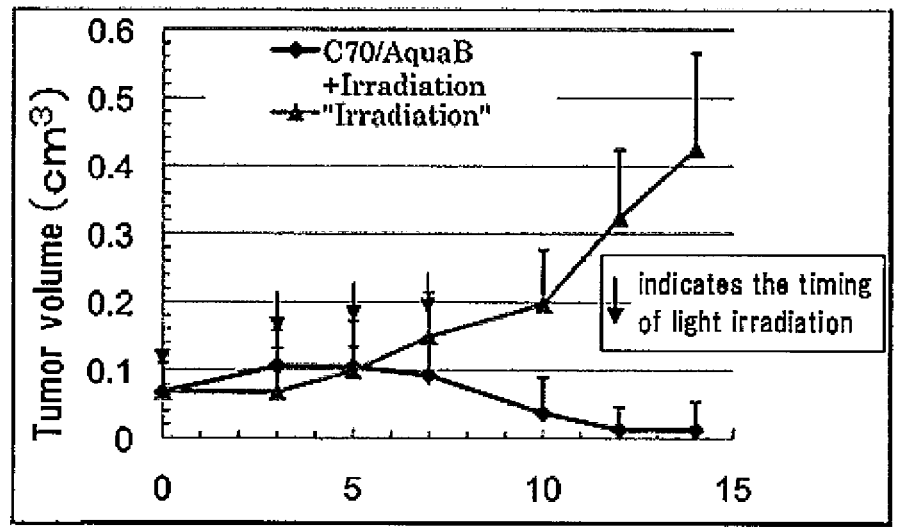
FIG. 5 (A) is a graph showing that the tumor volume of tumor bearing mice was reduced by the administration of an aqueous AQUA β-fullerene (C70) complex solution followed by light irradiation.
Figure 5:
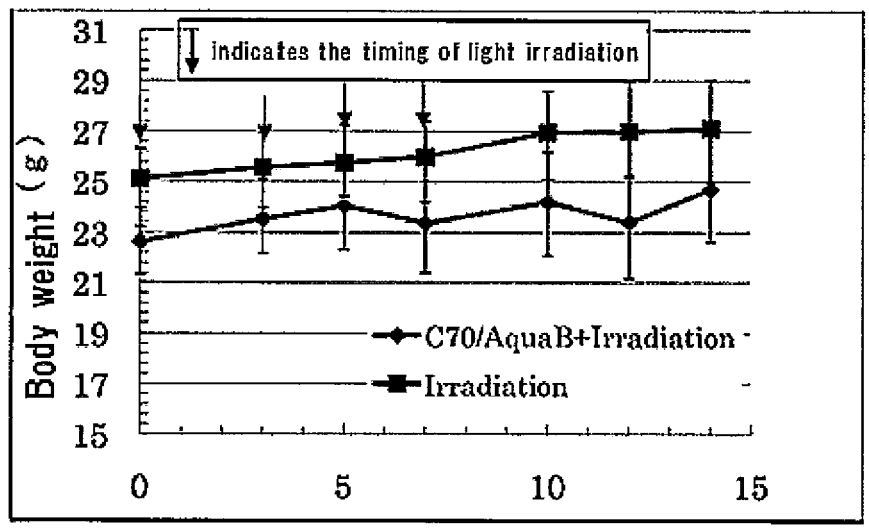

Transition of the tumor volume is shown in FIG. 5 (A). The administration of the aqueous AQUA β-fullerene (C70) complex solution markedly reduced the tumor volume.

Transition of the body weight of the mice is shown in FIG. 5 (B). The body weight slightly increased in both groups.

The results revealed that the AQUA β-fullerene (C70) complex exhibited toxicity only to tumor cells and brought about an anti-tumor effect, while did not affect normal cells.

Example 4 and Comparative Example 5

Water Solubilization of Boron Cluster Compound (m-carborane) by High Speed Vibration Milling m-carborane was mixed with AQUA β (DAISO Co., Ltd.) or sizofuran (SPG) (Mitsui Sugar Co., Ltd.) in the predetermined amounts shown in Table 3 below. The mixture was placed with an agate milling ball in an agate milling jar, and high speed milling was performed with a mixer mill (MM200, Retsch Co., Ltd.) at 25 Hz for 25 minutes. Next, 10,000 parts by weight of water was added to 1 part by weight of the mixture, and the mixture was stirred with a magnetic stirrer at room temperature for two days and further agitated with a vortex mixer for 2 hours. Centrifugation (25° C., 14,000 rpm, 20 minutes) was performed, and the supernatant was filtrated through a 0.45 μm membrane filter. The boron concentration of the filtrate was measured with an ICP atomic emission spectrometer for evaluation of the degree of water solubility. The results are shown in Table 3 below.

TABLE 3

| | AQUA β (mg) | Sizofiran (mg) | m-carborane (mg) | Boron concentration (ppm) |
|---|---|---|---|---|
| Example 2 | 12.2 | — | 17.8 | 0.62 |
| Comparative Example 4 | — | 8.07 | 6.14 | 0.18 |

As apparent from Table 3, the boron concentration of the aqueous boron cluster solution prepared using AQUA β was 3 times higher or more than that of the solution prepared using sizofuran. The results revealed that m-carborane was efficiently solubilized in water when complexed with a β-1,3-1,6-D-glucan having a degree of branching of 50% or more.

Example 5 and Comparative Example 6

Water Solubilization of Boron Cluster Compound (m-carborane) by DMSO-Renature Method m-carborane was mixed with AQUA β (DAISO Co., Ltd.) as a β-1,3-1,6-D-glucan or sizofuran (SPG) (Mitsui Sugar Co., Ltd.) in the predetermined amounts shown in Table 4 below. The mixture was dissolved in DMSO (5 mL). Ultrasonication was performed with an ultrasonic bath for 1 hour to give a dispersion. When dissolved in DMSO, the β-1,3-1,6-D-glucan, which usually exists as a triple stranded helix structure, was dissociated into separate random coils.

Next, Milli Q water was added in amounts of 1 mL×5 times, 2 mL×5 times, and 5 mL×6 times, in this order, at intervals of 1 minute to increase the water content, thereby reconstructing the triple stranded helix formed by hydrophobic interaction and allowing m-carborane, which is hydrophobic, to be taken in the hydrophobic pockets in the triple stranded helix. In this way, water solubilization of m-carborane was attempted.

Next, DMSO was removed by dialysis (MWCO=3,500). After recovered, the dialyzed solution was concentrated with an evaporator. The boron concentration was measured with an ICP atomic emission spectrometer for evaluation of the degree of water solubility. The results are shown in Table 4 below.

TABLE 4

| | AQUA β (mg) | Sizofiran (mg) | m-carborane (mg) | Boron concentration (ppm) | Solution volume (mL) | Boron-solubilizing capability (%) |
|---|---|---|---|---|---|---|
| Example 3 | 12.0 | — | 6.40 | 0.91 | 5.0 | 0.095 |
| Comparative Example 5 | — | 8.21 | 6.14 | 0.16 | 3.5 | 0.012 |

The results of the water solubilization by the non-protonic solvent revealed that AQUA β, which is a β-1,3-1,6-D-glucan having a degree of branching of 50% or more, has an about 8 times higher capability of water-solubilizing a boron cluster compound than sizofuran.

Example 6

Solubilization of Single-Walled Carbon Nanotube

Preliminary dispersion was performed by dispersing 1.0 mg of a single-walled carbon nanotube (SWNT) (Carbon Nanotechnology, Inc.) in 0.5 mL of DMSO, and performing ultrasonic irradiation. An amount of 1.0 mL of AQUA β (DAISO Co., Ltd.) in a DMSO solution (2.0 mg/mL) was added and ultrasonic irradiation was further performed for 1 hour. The obtained dispersion was added to 1.5 mL of distilled water. To the dispersion, 35 mL of distilled water was further added and the solution was allowed to stand for one day to renature the AQUA β. It was observed by visual inspection that the solution was uniform at that point. Centrifugation (8,000 rpm, 60 minutes) was performed to recover the complex as a precipitate, the supernatant was removed, and the precipitate was redispersed in distilled water. This procedure was repeated 3 times for removal of uncombined polysaccharides and replacement of the solvent with water. Thus a solution in which the SWNT was dispersed in 5 mL of distilled water was obtained.

Figure 6:
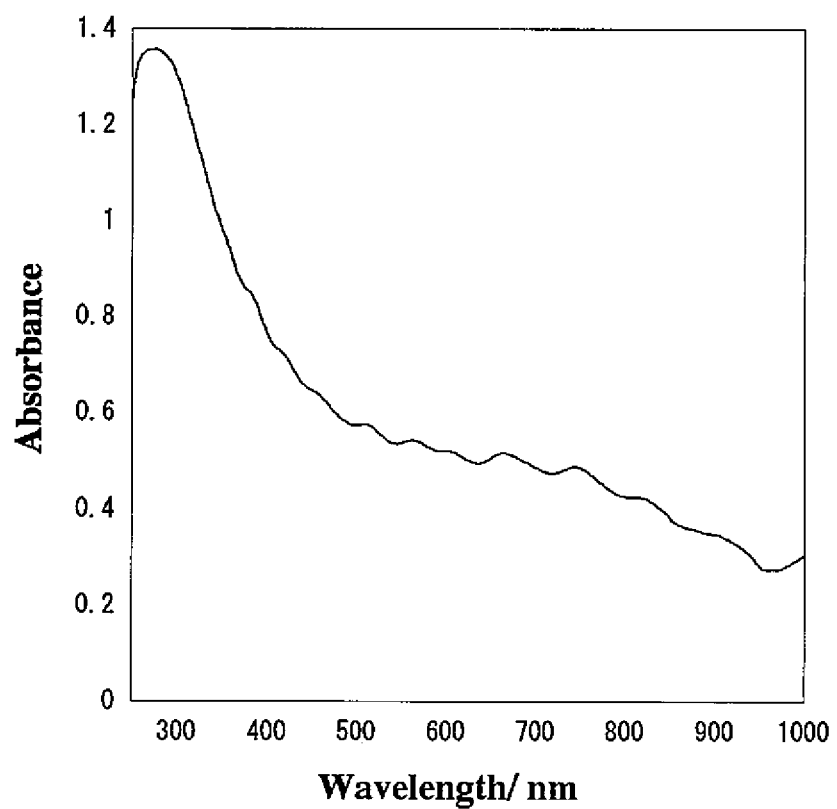
FIG. 6 is a UV-Vis-NIR spectrum of an aqueous AQUA β/SWNT complex obtained in Example 6. The measurement conditions were as follows: optical path length: 0.5 cm; solvent: $D_2O$; and room temperature.

The UV-Vis-NIR spectrum of the aqueous complex solution is shown in FIG. 6. The absorption band extending to near the infrared region, which band is unique to SWNTs, revealed that the SWNT was dispersed in water due to AQUA β. From the absorbance at 500 nm ($Abs_{500}$=0.575), the concentration of the dissolved SWNT is estimated at 5.0 mg/mL. This value indicates that, in comparison with dispersion using sizofiran (2.5 mg/mL), the dispersibility was markedly improved up to 2-fold. The improvement in the dispersibility seems to be attributed to the fact that AQUA β has a higher proportion of side chains than sizofuran.

Figure 7:
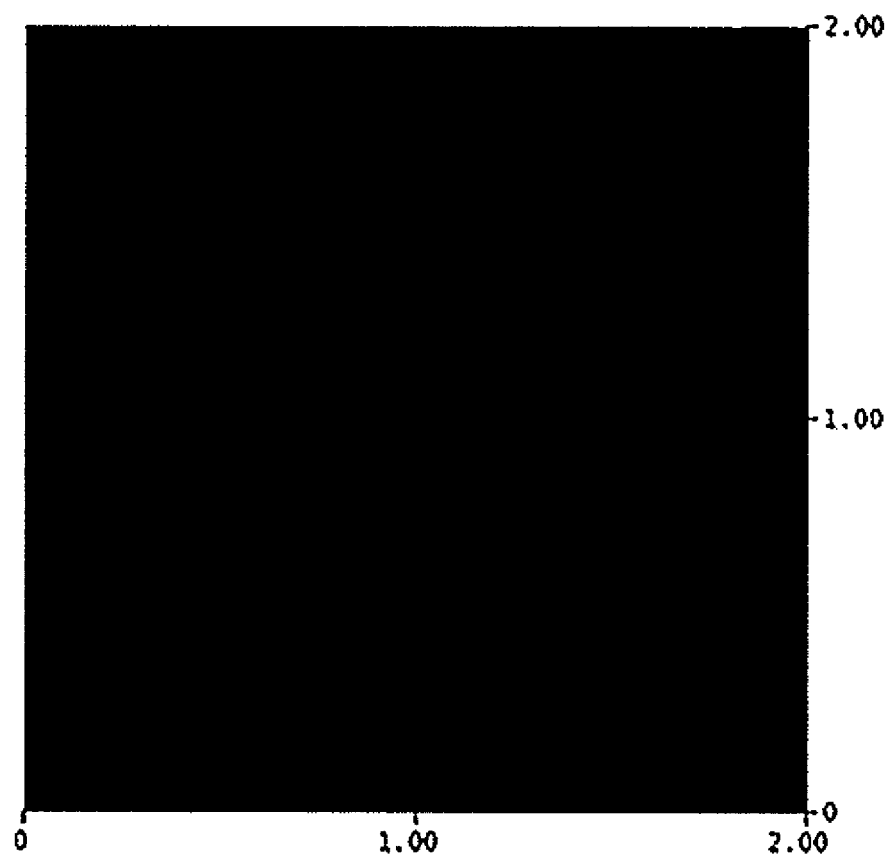
FIG. 7 is an AFM image of the AQUA β/SWNT complex obtained in Example 6.

Next, the obtained aqueous solution was cast on a mica substrate and the form of the complex was examined. The image is shown in FIG. 7. As observed in the image, the surface of the SWNT is coated with AQUA β. The AQUA β seems to have covered the surface of the SWNT in a spiral manner. The AQUA β layer constructed on the SWNT surface in this manner inhibited aggregations of the SWNTs, thereby achieving dispersion of the SWNTs in a high concentration.

The results revealed that AQUA β, which is a β-1,3-1,6-D-glucan having a degree of branching of 50% or more, was able to impart high dispersibility to a single-walled carbon nanotube.

Example 7

Solubilization of Multi-Walled Carbon Nanotube

The experiment was carried out in the same manner as in Example 6 except that a multi-walled carbon nanotube was used instead of the single-walled carbon nanotube.

That is, preliminary dispersion was performed by dispersing 15 mg of a multi-walled carbon nanotube (MWNT) (Carbon Nanotechnology, Inc.) in 1.0 mL of DMSO, and performing ultrasonic irradiation. An amount of 3.0 mL of AQUA β (DAISO Co., Ltd.) in a DMSO solution (5 mg/mL) was added and ultrasonic irradiation was further performed for 1 hour. The obtained dispersion was added to 4.0 mL of distilled water to renature the AQUA β. It was observed by visual inspection that the solution was uniform at that point. Centrifugation (8,000 rpm, 60 minutes) was performed to recover the complex as a precipitate, the supernatant was removed, and the precipitate was redispersed in distilled water. This procedure was repeated 3 times for removal of uncombined polysaccharides and replacement of the solvent with water. After that, 3.0 mL of distilled water was added to give a 5.0 mg/mL dispersion of the MWNT.

The results revealed that AQUA β, which is a β-1,3-1,6-D-glucan having a degree of branching of 50% or more, was also able to impart high dispersibility to a multi-walled carbon nanotube.

Example 8

Preparation of Gel Using Solubilized Single-Walled Carbon Nanotube Dispersion To 2 mL of the single-walled carbon nanotube dispersion (5.0 mg/mL) obtained in Example 6 was added 1 mL of a 50 mg/mL aqueous solution of curdlan (Wako Pure Chemical Industries, Ltd.; β-1,3-D-glucan, molecular weight: 2,000, 000) in 1 N sodium hydroxide. The mixture was agitated with a vortex mixer for several tens of seconds. Immediately after agitation, an equivalent amount of 1 N hydrochloric acid was added and agitated in the same manner to adjust the pH to neutral. The prepared sample was applied to a glass plate at a consistent thickness and dried with a vacuum pump for 1 hour to give a gel-like dried matter.

Example 9

Preparation of Silver Nanoparticle Dispersion

Preliminary dispersion was performed by dispersing 1.0 mg of a silver nanoparticle (average particle diameter: 20 nm, DOWA electronics Materials Co., Ltd.) in 0.5 mL of DMSO, and performing ultrasonic irradiation. An amount of 1.0 mL of AQUA β (DAISO Co., Ltd.) in a DMSO solution (2.0 mg/mL) was added and ultrasonic irradiation was further performed for 1 hour. The obtained dispersion was added to 1.5 mL of distilled water. To the dispersion, 35 mL of distilled water was further added and the solution was allowed to stand for one day to renature the AQUA β. It was observed by visual inspection that the solution was uniform at that point. Centrifugation (8,000 rpm, 60 minutes) was performed to recover the complex as a precipitate, the supernatant was removed, and the precipitate was redispersed in distilled water. This procedure was repeated 3 times for removal of uncombined polysaccharides and replacement of the solvent with water. Thus a solution in which the SLANT was dispersed in 5 mL of distilled water was obtained.

Even when this solution was placed in a 10 mL glass tube with a screw cap (Nippon Electric Glass Co., Ltd.) and allowed to stand for one day, no precipitation occurred; thus the solution exhibited excellent dispersibility. The solution was further diluted with distilled water so that the silver content was 200 ppm and the ultraviolet and visible absorption spectrum of the obtained yellow transparent aqueous solution was measured. A sharp, peak at 420 nm, which is due to the plasmon absorption specific to silver nanoparticles, was observed in the absorption spectrum.

Example 10

Preparation of Gold Nanoparticle Dispersion

An amount of 100 mg of AQUA β (DAISO Co., Ltd.) was dissolved in 100 mL of deionized water. To this solution, 0.1 mmol (41.19 mg) of tetrachloroauric acid tetrahydrate was added. It was observed by visual inspection that the solution was uniform at that point.

Dimethylamino ethanol was added to the solution to advance reduction reaction, and the solution was stirred at room temperature for 3 hours.

Centrifugation (8,000 rpm, 60 minutes) of the solution was performed to recover the complex as a precipitate, the supernatant was removed, and the precipitate was redispersed in distilled water. This procedure was repeated twice for removal of dimethanolamine and residual ions. Thus a solution in which the nanoparticles were dispersed in 100 mL of distilled water was obtained. Even when 5 mL of this solution was placed in a 10 mL glass tube with a screw cap (Nippon Electric Glass Co., Ltd.) and allowed to stand for one day, no precipitation occurred; thus the solution exhibited excellent dispersibility. The solution was further diluted with distilled water so that the gold content was 200 ppm and the ultraviolet and visible absorption spectrum of the obtained red transparent aqueous solution was measured. A sharp peak at 530 nm, which is due to the plasmon absorption specific to gold nanoparticles, was observed in the absorption spectrum.

INDUSTRIAL APPLICABILITY

The hydrophobic cluster compound complex of the present invention, to which water solubility or water dispersibility has been imparted, is applicable as a medicine.

The invention claimed is:

1. A complex comprising
a hydrophobic cluster compound selected from the group consisting of a carborane, a fullerene, a carbon nanotube, a carbon nanocoil, and a microparticle, wherein the microparticle is an aggregation of at least one kind of metal atom selected from the group consisting of platinum, gold, silver, copper, titanium, zinc, iron, cobalt, magnesium, aluminum, and zirconium, and
a β-1,3-1,6-D-glucan having a degree of branching (a ratio of β-1,6 linkages to β-1,3 linkages) of 85 to 100%.

2. The complex according to claim 1, wherein the β-1,3-1, 6-D-glucan was produced by *Aureobasidium pullulans*.

3. The complex according to claim 1, wherein the β-1,3-1, 6-D-glucan was subjected to alkali treatment at a pH of 12 or higher followed by neutralization.

4. A production process for a complex comprising a hydrophobic cluster compound and a β-1,3-1,6-D-glucan, the process comprising the steps of
agitating a hydrophobic cluster compound selected from the group consisting of a carborane, a fullerene, a carbon nanotube, a carbon nanocoil, and a microparticle, wherein the microparticle is an aggregation of at least one kind of metal atom selected from the group consisting of platinum, gold, silver, copper, titanium, zinc, iron, cobalt, magnesium, aluminum, and zirconium, with a β-1,3-1,6-D-glucan having a degree of branching (a ratio of β-1,6 linkages to β-1,3 linkages) of 50 to 100% while maintaining the solid state, and
agitating the mixture with added water.

5. A production process for a complex comprising a hydrophobic cluster compound and a β-1,3-1,6-D-glucan, the process comprising the steps of
mixing, in a polar solvent, a hydrophobic cluster compound selected from the group consisting of a carborane, a fullerene, a carbon nanotube, a carbon nanocoil, and a microparticle, wherein the microparticle is an aggregation of at least one kind of metal atom selected from the group consisting of platinum, gold, silver, copper, titanium, zinc, iron, cobalt, magnesium, aluminum, and zirconium, and a β-1,3-1,6-D-glucan having a degree of branching (a ratio of β-1,6 linkages to β-1,3 linkages) of 50 to 100%, and
adding water to the obtained mixture and allowing the mixture to ripen.

6. The production process according to claim 4, wherein the β-1,3-1,6-D-glucan was produced by *Aureobasidium pullulans*.

7. The production process according to claim 4, wherein the β-1,3-1,6-D-glucan was subjected to alkali treatment at a pH of 12 or higher followed by neutralization.

8. The production process according to claim 5, wherein the β-1,3-1,6-D-glucan was produced by *Aureobasidium pullulans*.

9. The production process according to claim 5, wherein the β-1,3-1,6-D-glucan was subjected to alkali treatment at a pH of 12 or higher followed by neutralization.

* * * * *